(12) United States Patent
Ouwerkerk et al.

(10) Patent No.: US 9,706,942 B2
(45) Date of Patent: Jul. 18, 2017

(54) WEARABLE DEVICE AND A METHOD OF MANUFACTURING THE SAME

(75) Inventors: Martin Ouwerkerk, Culemborg (NL); Joanne Henriëtte Desirée Monique Westerink, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 22 days.

(21) Appl. No.: 14/233,036

(22) PCT Filed: Jul. 10, 2012

(86) PCT No.: PCT/IB2012/053514
§ 371 (c)(1),
(2), (4) Date: Jan. 15, 2014

(87) PCT Pub. No.: WO2013/011416
PCT Pub. Date: Jan. 24, 2013

(65) Prior Publication Data
US 2014/0155724 A1    Jun. 5, 2014

Related U.S. Application Data (60) Provisional application No. 61/509,599, filed on Jul. 20, 2011.

(51) Int. Cl.
*A61B 5/053* (2006.01)
*A61B 5/05* (2006.01)
*A61B 5/00* (2006.01)

(52) U.S. Cl.
CPC .............. *A61B 5/0531* (2013.01); *A61B 5/05* (2013.01); *A61B 5/053* (2013.01); *A61B 5/681* (2013.01); *A61B 5/6814* (2013.01); *A61B 5/6824* (2013.01); *A61B 5/6829* (2013.01); *A61B 5/6831* (2013.01); *A61B 5/6834* (2013.01); *A61B 2562/164* (2013.01)

(58) Field of Classification Search
CPC ..... A61B 5/0531; A61B 5/681; A61B 5/6824; A61B 5/6831; A61B 5/6834
USPC ......................................... 600/386, 390, 547
See application file for complete search history.

(56) References Cited

U.S. PATENT DOCUMENTS

| 3,870,034 | A  |   | 3/1975  | James |         |
|-----------|----|---|---------|-------|---------|
| 3,954,100 | A  | * | 5/1976  | Sem-Jacobsen | 600/393 |
| 4,082,087 | A  | * | 4/1978  | Howson | 600/391 |
| 4,365,637 | A  | * | 12/1982 | Johnson | 600/547 |
| 6,577,897 | B1 | * | 6/2003  | Shurubura et al. | 600/547 |

(Continued)

FOREIGN PATENT DOCUMENTS

| JP | 03118037 A | 5/1993 |
|----|------------|--------|
| JP | 2002369806 A | 12/2002 |

(Continued)

*Primary Examiner* — Lee S Cohen (57) ABSTRACT

The present invention relates to a wearable device (10) wearable by a user for measuring skin conductance of the user (1), the wearable device comprising at least two skin conductance electrodes (12) for contacting skin (2) of the user, and an elastic material portion (14) which surrounds the skin conductance electrodes (12) and forms a material surface (16). The elastic material of the elastic material portion (14) is non-permeable for gaseous and liquid substances. The present invention further relates to a method of manufacturing such a wearable device (10).

13 Claims, 10 Drawing Sheets

(56) References Cited

U.S. PATENT DOCUMENTS

| | | |
|---|---|---|
| 7,052,472 B1 | 5/2006 | Miller et al. |
| 7,308,294 B2 | 12/2007 | Hassonjee et al. |
| 2004/0077969 A1 | 4/2004 | Onda et al. |
| 2006/0084855 A1 | 4/2006 | Teschner et al. |
| 2008/0214901 A1 | 9/2008 | Gehman et al. |
| 2009/0076362 A1* | 3/2009 | Jaatinen .................. 600/372 |
| 2009/0137892 A1* | 5/2009 | Leftly et al. ............. 600/390 |
| 2010/0268056 A1 | 10/2010 | Picard et al. |
| 2011/0319786 A1* | 12/2011 | Rebello et al. ........... 600/547 |
| 2014/0155724 A1 | 6/2014 | Ouwerkerk et al. |

FOREIGN PATENT DOCUMENTS

| | | |
|---|---|---|
| JP | 2005261464 A | 9/2005 |
| JP | 2007525269 | 9/2007 |
| JP | 2008237271 A | 10/2008 |
| JP | 2010222396 A | 10/2010 |
| WO | 2004056418 A1 | 7/2004 |
| WO | 2009017808 A1 | 2/2009 |

\* cited by examiner

WEARABLE DEVICE AND A METHOD OF MANUFACTURING THE SAME

CROSS-REFERENCE TO PRIOR APPLICATIONS

This application is the U.S. National Phase application under 35 U.S.C. §371 of International Application No. PCT/IB2012/053514, filed on Jul. 10, 2012, which claims the benefit of U.S. Provisional Patent Application No. 61/509,599 filed on Jul. 20, 2011. These applications are hereby incorporated by reference herein.

FIELD OF THE INVENTION

The present invention relates to a wearable device wearable by a user for measuring skin conductance of the user, the wearable device comprising at least two skin conductance electrodes, in particular dry electrodes, for contacting skin of the user (and for measuring skin conductance in between). The present invention further relates to a method of manufacturing such wearable device.

BACKGROUND OF THE INVENTION

It is known that skin conductance of a user is related with the level of arousal of the user. Everything that emotionally touches the user activates the sweat glands in the skin, leading to a better conductor path through the skin. For example, in a known lie detector or polygraph, a skin conductance sensor connected to the palm of the hand or the fingers is used.

However, the skin conductance can also be measured on other parts of the body of the user. Indeed, in many locations the skin conductance could be measured, even though with a less fine structure and at a lower signal-to-noise ratio. For example, skin conductance can be measured on the wrist of the user using a (skin conductance) wristband.

Using a skin conductance wristband is different from the traditional skin conductance measurement methods in that the period of measurement can be much longer. It may extend over several weeks. This requires the use of an interface between wristband and skin that causes no problems to the user wearing the wristband, such as skin irritation or skin coloration.

US 2010/0268056 A1 discloses a flexible wrist/hand band with a sensor to detect electrodermal activity (EDA). The circuitry for the EDA sensor fits, and is secured within a hydrophobic pouch on the band. A hydrophobic, breathable material is used to form the pouch for circuitry, and to form parts of the wearable band. The electrodes are hosted by a flexible, breathable material. In some embodiments, the material used for this flexible, breathable material may be the same as the breathable, hydrophobic material used to form the pouch. The wrist is not a standard location for measuring EDA since the sweat glands there tend to be less sensitive than those on the palm of fingers, where EDA is traditionally measured. This issue, coupled with the use of dry electrodes, means that it usually takes at least 15 minutes (depending on humidity and the individual's temperature) before the moisture built up between the skin and electrodes is sufficient to show a range of responsiveness on the wrist.

A problem with such a wristband can be that for a certain percentage of users, the skin conductance measurement signal is too low to register. Thus, for some users a very poor or no skin conductance measurement at all may be obtained.

SUMMARY OF THE INVENTION

It is an object of the present invention to provide, in particular for long-term use or measurement, a wearable device wearable by a user for measuring skin conductance of the user which provides an improved measurement of the skin conductance, in particular for a variety of different users having different skin types, or basically for each user, and/or in a variety of ambiences. It is a further object of the present invention to provide a method of manufacturing such a wearable device.

In a first aspect of the present invention, a wearable device wearable by a user for measuring skin conductance of the user is presented that comprises at least two skin conductances electrodes for contacting skin of the user, and an elastic material portion which surrounds the skin conductance electrodes and forms a material surface. The elastic material of the elastic material portion is non-permeable for gaseous and liquid substances.

In a further aspect of the present invention a method of manufacturing a wearable device wearable by a user for measuring skin conductance of the user is presented, the method comprising providing at least two skin conductance electrodes for contacting skin of the user, and forming an elastic material portion which surrounds the skin conductance electrodes and forms a material surface. The elastic material of the elastic material portion is non-permeable for gaseous and liquid substances.

The basic idea of the invention is to provide a wearable device, in particular a wristband, handband, ankleband or the like, comprising an elastic material portion surrounding (in particular circumferentially enclosing) the skin conductance electrodes which is made of an elastic material which is non-permeable for gaseous and liquid substances such that a fluid film is generated between the skin and the electrodes when the wearable device is worn by the user. In particular, the elastic material is non-permeable for any gaseous and liquid substances, for example including water, water vapor and/or air. As the elastic material is non-permeable for air, the elastic material is in particular non-breathable. As the elastic material is non-permeable for water, the elastic material is in particular non-water-permeable. The fluid film is made of (human) sweat of the user from sweat glands. By using the elastic material which is non-permeable for gaseous and liquid substances it is achieved that the fluid loss through re-uptake of the skin plus evaporation of fluid to the outside ambient is lower than the fluid generation through the sweat glands. In this way, a reliable measurement of the skin conductance is provided, basically for each user and in a variety of ambiences. The skin conductance values are always within the measurable range. Thus, the number of so-called "non-responders" when measuring the skin conductance can be substantially reduced or eliminated. The stable fluid film causes a stable microclimate in the immediate surroundings or vicinity of the skin conductance electrodes (in particular in between the electrodes). Thus, the use of the elastic material portion surrounding the skin conductance electrodes creates a moist microclimate causing the skin conductance measurement or sensor data to stay within a measurable range for basically all users for basically all of the time. A high skin conductance level for all skin types and all ambiences can thus be achieved.

Preferred embodiments of the invention are defined in the dependent claims. It shall be understood that the claimed method of manufacturing has similar and/or identical preferred embodiments as the claimed wearable device and as defined in the dependent claims.

In one embodiment the elastic material portion is arranged such that an air pocket is sealed off in the vicinity of the skin conductance electrodes, when the skin conductance electrodes contact the skin of the user. By sealing off an air pocket, a hermetic sealing of a small area surrounding the skin conductance electrodes from the outside atmosphere is achieved. This improves the skin conductance measurement even further.

In one embodiment the elastic material is a polymer or rubber. These materials are particularly suitable to be used as the elastic material.

In another embodiment the elastic material is a polyurethane resin mixture at a specific mixture ratio. To use a very specific mixture ratio of the polyurethane resin has shown to influence the material characteristics, in particular the permeability for gaseous and liquid substances.

In a variant of this embodiment the polyurethane resin mixture is made of polyetherpolypol and 4,4'-diphenylmethane diisocyanate (also known as CAS 101-68-8) at a ratio of about 100:40. This specific mixture of polyurethane resins has been shown to be particularly suitable. In particular, this material is known as type 6120, for example manufactured by MTT Technologies Group. In another embodiment the skin conductance electrodes protrude from the material surface. The protrusion of the skin conductance electrodes enables to create the sealed off air pocket.

In a variant of this embodiment the skin conductance electrodes protrude between 50 to 1000 micrometer from the material surface, in particular between 100 and 700 micrometer. These protrusion distances have shown to be particularly suitable to seal off the air pocket.

In another embodiment the wearable device further comprises a housing portion made of a non-elastic material. Using a non-elastic material for the housing portion provides for a more robust device.

In a variant of this embodiment the elastic material of the elastic material portion is a polyurethane resin mixture at a specific mixture ratio, and wherein the housing portion is made of the same polyurethane resin mixture at a different mixture ratio. By using the same polyurethane resin mixture at different mixture ratios, the manufacturing method is simplified and/or the attachment between the elastic material portion and the housing portion is improved.

In another embodiment the wearable device further comprises a skin conductance measuring unit adapted to measure the skin conductance of the user between the skin conductance electrodes. In this way, a skin conductance sensor is provided. The skin conductance sensor is integrated into the wearable device, such as for example a wristband, handband, ankleband or the like. In particular, the skin conductance measuring unit or sensor can comprise a voltage generator for applying a voltage between the at least two skin conductance electrodes, a sensing unit for sensing a current between the at least two electrodes, and/or a calculating unit for calculating the skin conductance based on the sensed current. The measured skin conductance over time forms skin conductance data.

In a variant of this embodiment the wearable device is further adapted to determine a stressful period or event based on the measured skin conductance (skin conductance data) of the user. In this way stressful periods in the user's life can be distinguished. A stressful period or event can for example be determined based on a particular rising slope and/or a particular down slope of the skin conductance (skin conductance data). For example, a stressful period or event can be detected by detecting a peak of the skin conductance (skin conductance data), in particular a peak with a steeper rising slope and a more gentle down slope. In one variant the wearable device itself comprises a processing unit configured to determine a stressful period or event. In an alternative variant the processing unit is a separate part and the wearable device comprises a (wireless) transmitter for transmitting the skin conductance data to the separate part.

In a variant of this embodiment the skin conductance measuring unit is at least partly arranged in the housing. In this way, the electric circuitry of the skin conductance measuring unit can be protected.

In a further embodiment the elastic material has an elasticity that is sufficient to follow the shape of the wrist of the user. In this way, the wearable device can be put around the wrist of the user. Thus, the wearable device is a wristband adapted to be put around the wrist of the user. Measuring skin conductance on the wrist using a wristband is an unobtrusive way of measurement.

In a further embodiment, the skin conductance electrodes are arranges so as to contact the volar side of the wrist. At the volar side of the wrist there is normally not a lot of hair. Thus, a better measurement of the skin conductance can be provided.

In a further embodiment the method further comprises the step of forming a housing portion made of a non-elastic material. In this way, a more robust device can be provided.

In a further embodiment the elastic material portion is formed by injection moulding. This presents an especially easy way of forming the elastic material portion, in particular when the elastic material is a polymer or rubber.

In a further embodiment, in a first injection moulding step the housing portion is formed, and in a second injection moulding step the elastic material portion is formed. This provides for a two-step injection moulding process, which is particularly advantageous.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
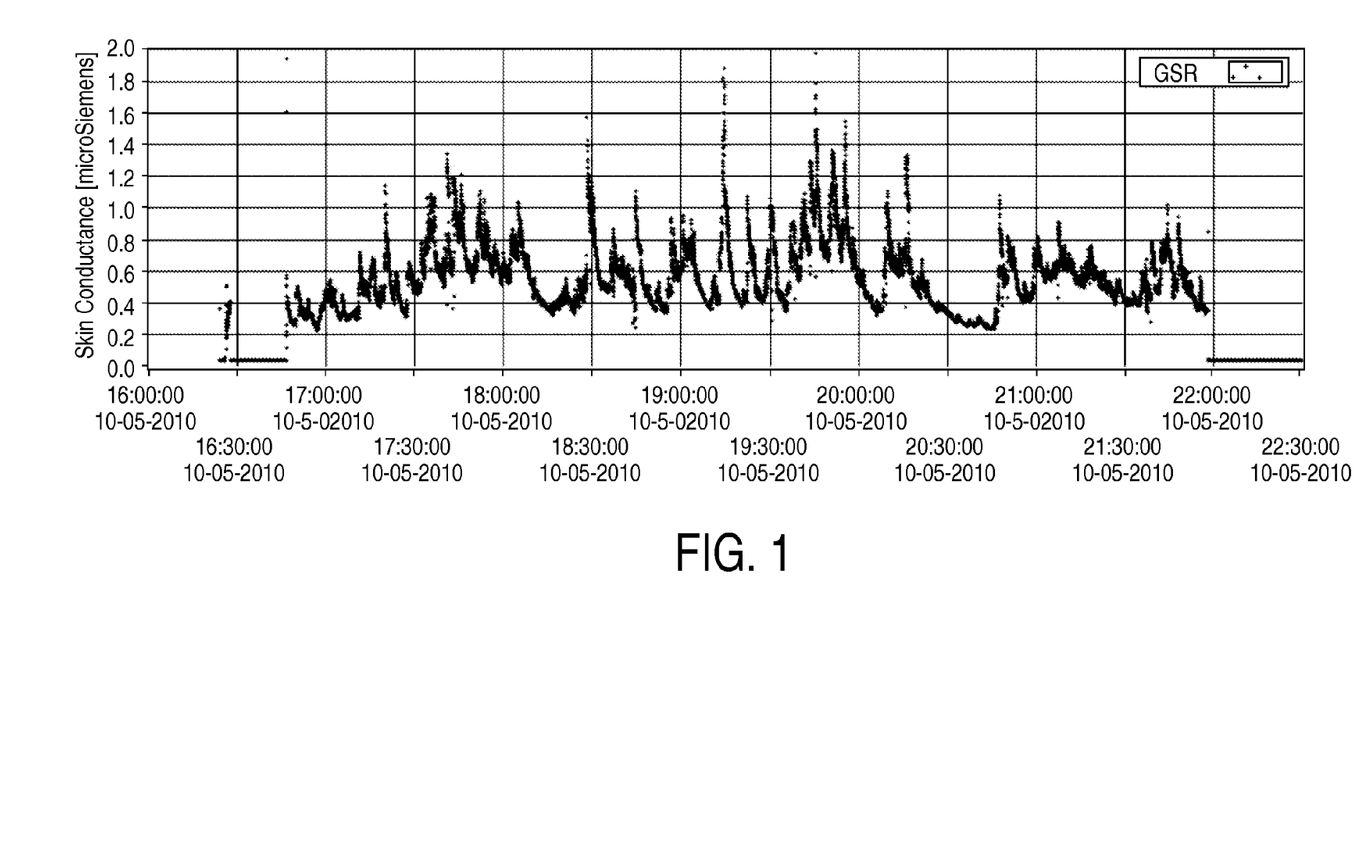
FIG. 1 shows a first example of a skin conductance trace measured by a skin conductance measuring unit or sensor.

FIG. 1 shows a first example of a skin conductance trace measured by a skin conductance measuring unit or sensor, for example integrated in or measured with the wearable device disclosed herein. The x-axis denotes the time t over a period of several hours, here from about 16 o'clock (4 p.m.) to 22.30 o'clock (10.30 p.m.). Thus, a skin conductance trace is formed over several hours. In FIG. 1, the y-axis denotes the measured skin conductance values, also called galvanic skin response (GSR) or electrodermal activity (EDA), measured in μS. Each point of the skin conductance phase indicates the skin conductance value sensed by the skin conductance measuring unit or sensor at that specific point in time t. Skin conductance (or GSR or EDA), is a measure of the electrical conductance of the skin, which varies with its moisture level, thus the sweat gland activity. Emotional events show as peaks with a steeper rising slope and a more gentle down slope. In FIG. 1, each peak corresponds to a response of the sympathetic nervous system to an emotionally arousing event (communicated via the vagus nerve to the sweat glands of the skin).

The skin conductance is the reverse of the electrical resistance of the skin. The stratum corneum of the skin forms an electrical barrier, causing the skin resistance to be high. Thus, the skin resistance consists mainly of the resistance of the stratum corneum. The sweat glands function as conductive channels in this barrier, the stratum corneum. There is a link or relationship between the number of sweat glands and the skin conductance value.

Figure 2:
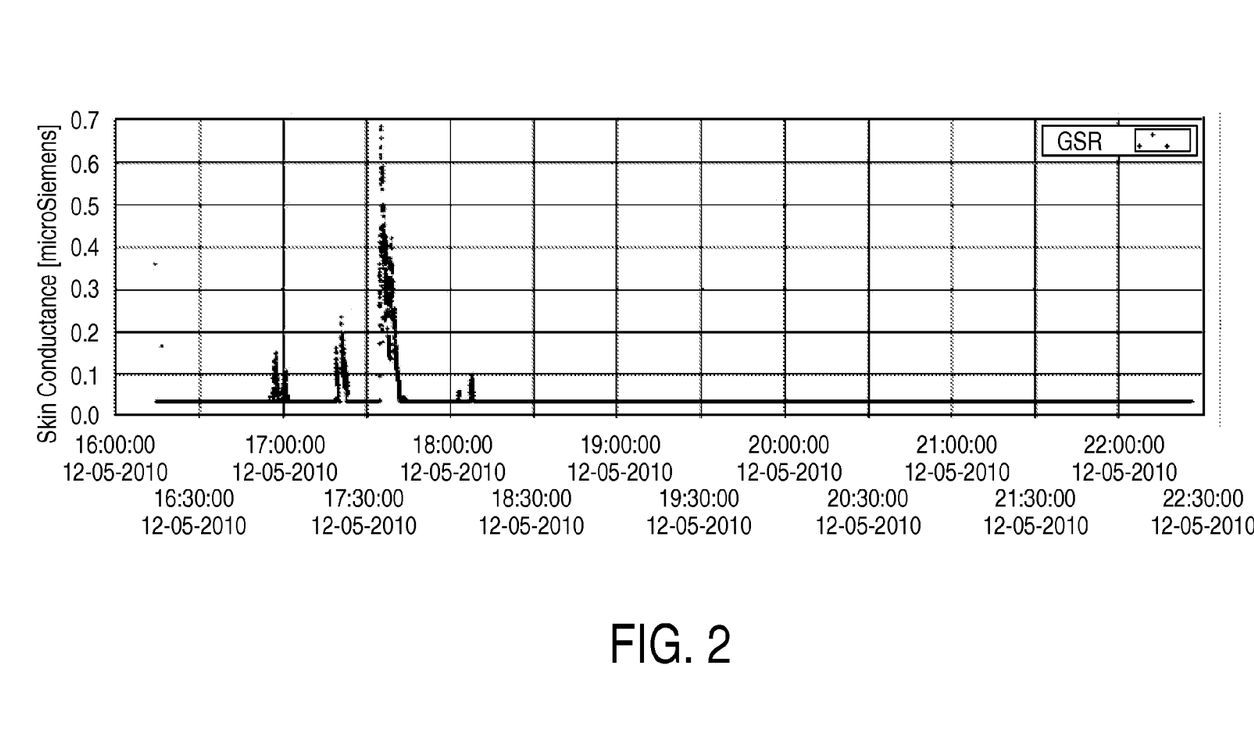
FIG. 2 shows a second example of a skin conductance trace measured by a skin conductance measuring unit or sensor, not according to the invention.

However, for a certain percentage of users, the skin conductance measuring value or signal can be too low to register. FIG. 2 shows such an example of a skin conductance trace measured by a skin conductance measuring unit or sensor, not according to the invention. The skin conductance values or signal shown in FIG. 2 are too low to measure for a large part of the time. Only the effects of strong emotional events or stressors are visible in the skin conductance trace of FIG. 2.

The range of skin conductances over the entire population turns out to be very large. For example, a user with a dry skin tends to have such a low skin conductance that, when measuring the skin conductance of the user, the signal is below the range of the skin conductance measuring unit or sensor. An effect of dry skin is apparently that the activity of sweat glands is so low that only strong emotional events or stressors evoke a skin conductance response. In cold and/or dry ambient the skin tends to dry out, which in the same way yields a worsening of the skin conductance response to emotional events or stressors.

Figure 3:
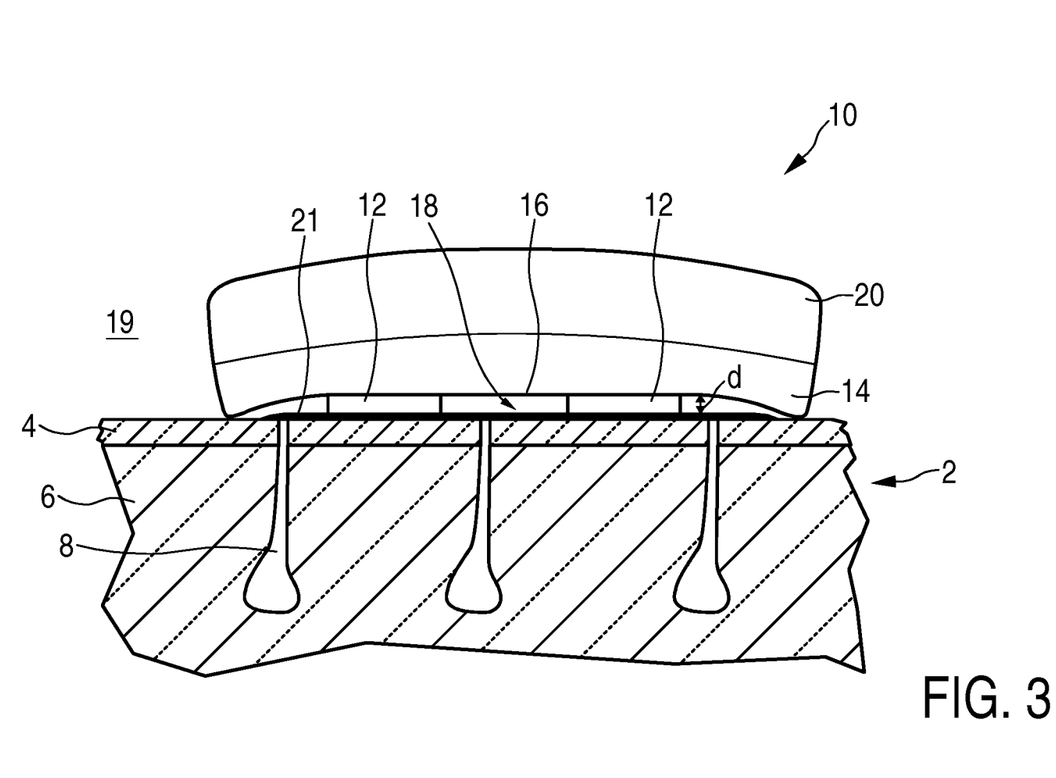
FIG. 3 shows a cross-section of a wearable device according to an embodiment.

FIG. 3 shows a cross section of a wearable device 10, wearable by a user and for measuring skin conductance of the user, according to an embodiment. The wearable device 10 comprises two skin conductance electrodes 12 for contacting skin 2 of the user. In the embodiment of FIG. 3, exactly two skin conductance electrodes 12 are used. As can be seen in FIG. 3, the skin 2 comprises the stratum corneum as its top layer. Further, the skin 2 comprises lower skin layers 6. Sweat glands 8 extend from the lower skin layers 6 through the stratum corneum 4 to the top surface of the skin 2. Thus, the sweat glands 8 function as conductive channels in the stratum corneum 4.

The wearable device 10 comprises an elastic material portion 14 which surrounds the skin conductance electrodes 12 and forms a material surface 16. In particular the elastic material portion 14 circumferentially encloses the electrodes 12. The elastic material of the elastic material portion 14 is non-permeable for gaseous and liquid substances. For example, the elastic material is non-permeable for water, water vapor and/or air. In this way a fluid film 21 is generated between the skin 2 and the electrodes 12 when the wearable device 10 is worn by the user. The fluid film 21 is made of (human) sweat of the user from sweat glands 8. It is achieved that the fluid loss through re-uptake of the skin 2 (or stratum corneum 4) plus evaporation of fluid to outside ambient 19 is lower than the fluid generation through the sweat glands 8. In particular, as the elastic material is non-permeable for air, the elastic material is non-breathable. In particular, as the elastic material is non-permeable for water, the elastic material is in particular non-water-permeable. In this way, a stable microclimate in the immediate surroundings or vicinity of the skin conductance electrodes 12 can be achieved. Thus, the use of the elastic material portion 14 surrounding the skin conductance electrodes 12 creates a moist microclimate, causing the skin conductance measurement or sensor data to stay within a measurable range for basically all users for basically all of the time. A high skin conductance level for all skin types and all ambiences can thus be achieved. The fluid film 21 is in particular formed in an area between the two electrodes 12. The elastic material (e.g. polymer or rubber) can thus be in between the electrodes 12.

The elastic material portion 14 is arranged such that an air pocket 18 is sealed off in the vicinity of the skin conductance electrodes 12, when the skin conductance electrodes 12 contact the skin 2 of the user, as shown in FIG. 3. By sealing off the air pocket 18, a hermetic sealing of a small area surrounding the skin conductance electrodes 12 from the outside atmosphere 19 is achieved. The air pocket 16 is in particular formed in an area between the two electrodes 12.

The elastic material can in particular be a polymer or a rubber. More specifically, the elastic material can be a polyurethane resin mixture at a specific mixture ratio, such as for example a polyurethane resin mixture made of polyetherpolypol and 4,4'-diphenylmethane diisocyanate (also known as CAS 101-68-8) at a ratio of about 100:40. This material is also known as type 6120, for example manufactured by MTT Technologies Group. The elastic material in particular has an elasticity that is sufficient to follow the shape of the wrist of the user. In this way, the wearable device 10 can be provided as a wristband adapted to be put around the wrist of the user.

As can be seen in FIG. 3, the wearable device 10 when worn by the user is pressed against the skin 2 of the user, such that the edges of the wearable device 10 or elastic material portion 14 are pressed against the skin 2. Further, referring to FIG. 3, the skin conductance electrodes 12 protrude from the material surface 16 by a distance d. In particular, the skin conductance electrodes 12 can protrude between 50 to 1000 micrometer from the material surface 16. More specifically, the distance can be between 100 and 700 micrometer. The skin conductance electrodes 12 can be two separate elements separated by a certain distance, as shown in FIG. 3. Alternatively, the two skin conductance electrodes can be integrated in a single element, as long as they are isolated from each other.

As can be seen in the embodiment of FIG. 3, the wearable device 10 further comprises a housing portion 20 made of a non-elastic material. In particular, if the elastic material of the elastic material portion 14 is a polyurethane resin mixture at a specific mixture ratio, as previously explained, the housing portion 20 can be made of the same polyurethane resin mixture but at a different mixture ratio.

Figure 4:
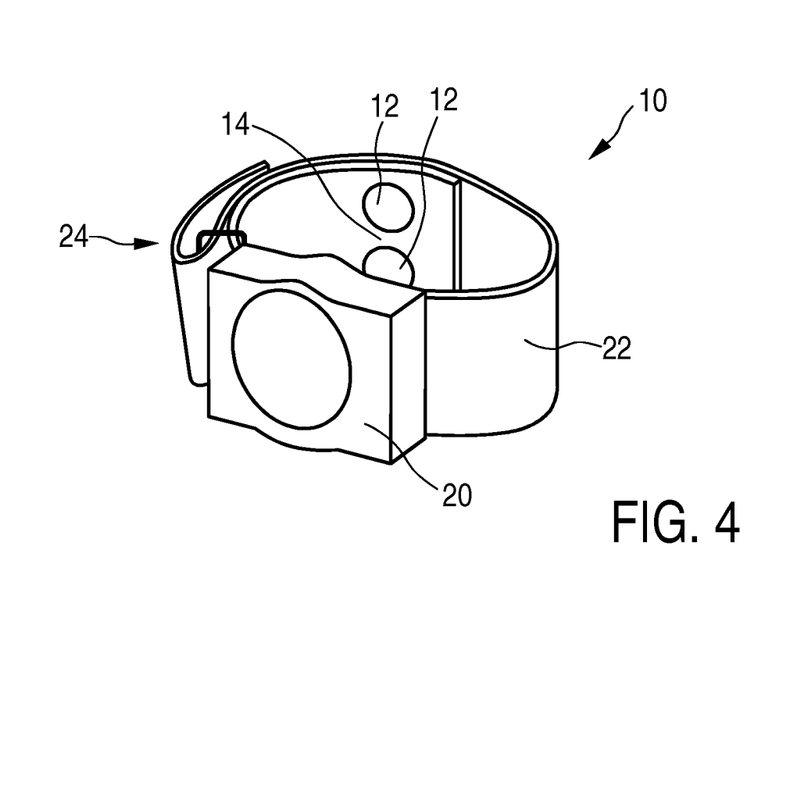
FIG. 4 shows a perspective view of a wearable device according to a first embodiment.
Figure 5:
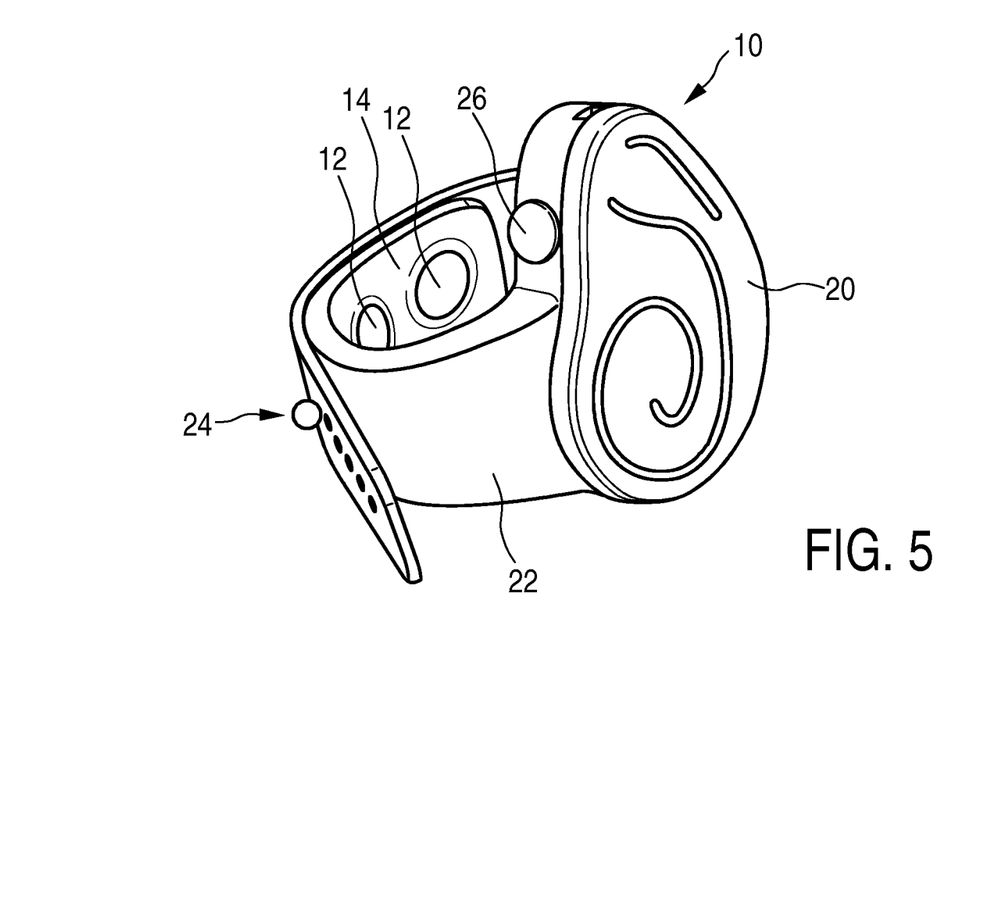
FIG. 5 shows a perspective view of a wearable device according to a second embodiment.

FIG. 4 shows a perspective view of a wearable device 10 according to a first embodiment. FIG. 5 shows a perspective view of a wearable device according to a second embodiment. Each of the wearable devices 10 shown in FIG. 4 and FIG. 5 can be the wearable device 10 as explained with reference to FIG. 3. In each of the embodiments of FIG. 4 and FIG. 5 the wearable device is a wristband having a skin conductance measuring unit or sensor integrated therein. The wearable device 10 comprises a skin conductance measuring unit, wherein the skin conductance measuring unit is adapted to measure the skin conductance of the user between the two skin conductance electrodes 12.

In each of the embodiments of FIG. 4 and FIG. 5, the wearable device 10 in form of the wristband comprises a wristband material part 22 and a housing portion 20. The wristband material part 20 can loop around the wrist of the user. It will be understood that the wearable device 10 could also be worn around any other suitable body part, such as the ankle, foot or hand. In each of the embodiments of FIG. 4 or FIG. 5, two skin conductance electrodes 12 are integrated into the wristband material part 22. As already explained with reference to FIG. 3, the wearable device 10 comprises an elastic material portion 14 which surrounds the skin conductance electrodes 12 and forms a material surface. The elastic material of the elastic material portion 14 is non-permeable for gaseous and liquid substances, when the skin conductance electrodes 12 contact the skin (at the wrist) of the user. In this way a fluid film is generated between the skin and the electrodes 12 when the wearable device 10 is worn by the user. The fluid film is made of (human) sweat of the user from sweat glands. It is achieved that the fluid loss through re-uptake of the skin plus evaporation of fluid to the outside ambient is lower than the fluid generation through the sweat glands. Furthermore, the elastic material portion is arranged such that an air pocket is sealed off in the vicinity of the skin conductance electrodes 12, when the skin conductance electrodes 12 contact the skin (at the wrist) of the user.

In each of the embodiments shown in FIG. 4 and FIG. 5, the elastic material portion 14 is part of or forms the wristband material part 22. The wristband material part 22 can also comprise at least one additional material portion, such as for example a textile material portion. The additional material portion can be permeable for gaseous and/or liquid substances, in particular breathable. The elastic material portion 14 can be integrated in such an additional material portion. The skin conductance electrodes 12 can be arranged so as to contact the volar side of the wrist, where is normally not a lot of hair, when the wearable device 10 is put on or worn by the user. Thus, a better measurement of the skin conductance can be provided. Furthermore, on the volar side of the wrist the sweat gland density is lower than as for example in the palm of the hand. The device described herein, due to the formation of a stable fluid film, achieves a good fluid-generation-to-fluid-loss balance at the volar side of the wrist for example.

The wearable device 10 further comprises a skin conductance measuring unit adapted to measure the skin conductance of the user between the skin conductance electrodes 12. Thus, the wearable device 10 comprises a skin conductance sensor. In particular, the skin conductance measuring unit or sensor can comprise a voltage generator for applying a voltage between the at least two skin conductance electrodes, a sensing unit for sensing a current between the at least two electrodes, and/or a calculating unit for calculating the skin conductance based on the sensed current. The skin conductance measuring unit in the embodiment of FIG. 4 or FIG. 5 is arranged in the housing portion 20 made of a non-elastic material. In this way, the electric circuitry of the skin conductance measuring unit can be protected. The skin conductance electrodes 12 are connected to the skin conductance measuring unit by means of wires integrated in the wristband material part 22 in the embodiment of FIG. 4 or FIG. 5.

The measured skin conductance over time forms skin conductance data. The skin conductance data can for example be stored in a memory of the wearable device 10 or can be (wirelessly) transmitted to an external unit using a (wireless) transmitter. In one example, the wearable device 10 is further adapted to determine a stressful period or event based on the measured skin conductance data of the user. In this way stressful periods in the user's life can be distinguished. A stressful period or event can for example be determined based on a particular rising slope and/or a particular down slope of the skin data. For example, a stressful period or event can be detected by detecting a peak of the skin conductance data, in particular a peak with a steeper rising slope and a more gentle down slope. In one example the wearable device 10 comprises a processing unit configured to determine a stressful period or event. In another example the processing unit is a separate part and the wearable device 10 transmits the skin conductance data to the separate part via the (wireless) transmitter.

In the embodiment of FIG. 4 or FIG. 5, the wristband material part 22 forms a closed loop using the fastening portion 24. In the embodiment of FIG. 4, the fastening portion is in the form of a hook-and-loop fastener, also known as Velcro® fastener. In the embodiment of FIG. 5, the fastening portion 24 is in the form of a pin fastener, such as for example commonly used for a watch. It will be understood that any other suitable fastener portion 24 can be used. As shown in FIG. 5, the wearable device 10 can further comprise a button 26 at an outer surface. The button 26 can for example be used to turn the wearable device 10 on and/or off, or more particularly to turn the skin conductance measuring unit or sensor on and/or off.

Figure 6:
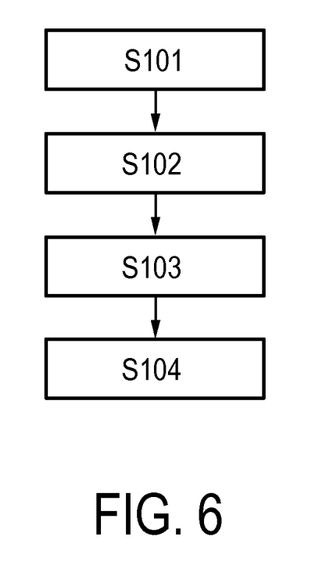
FIG. 6 shows a diagram of a method of manufacturing according to an embodiment.

FIG. 6 shows a diagram of a method of manufacturing according to an embodiment. The method is in particular for manufacturing a wearable device as previously described in connection with FIG. 3, FIG. 4 or FIG. 5 wearable by a user for measuring skin conductance of the user. In a first step, S101 a housing portion 20 made of a non-elastic material is formed, for example using a first injection moulding step. In an example, this non-elastic material can be a polyurethane resin mixture, as previously explained. In a second injection moulding step S102, the elastic material portion 14 is then formed. In an example, this elastic material can be a polyurethane resin mixture, in particular of type 6120, as previously explained.

Figure 7:
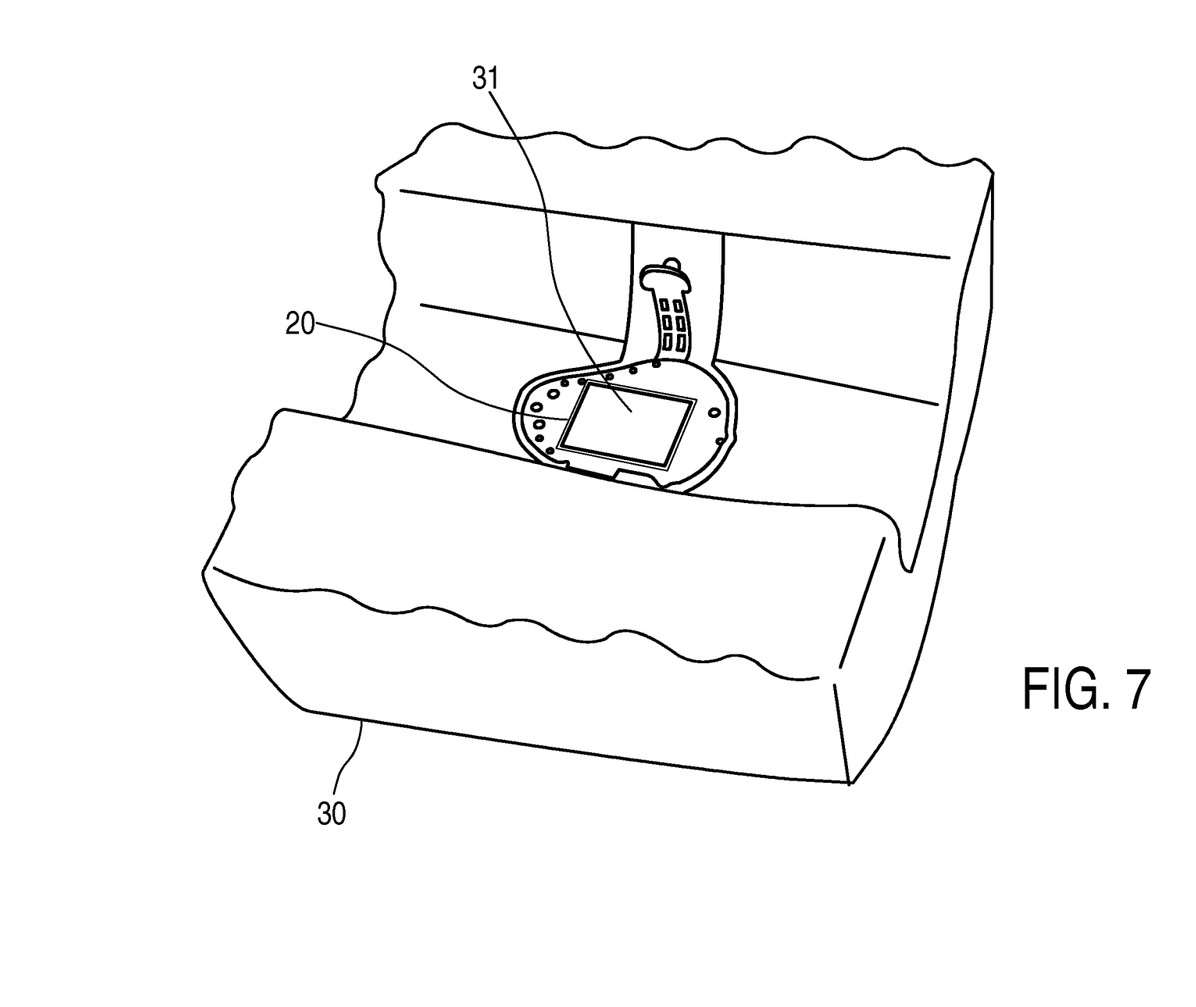
FIG. 7 shows a perspective view of part of the wearable device when performing the method of FIG. 6.

An example of such housing portion 20 is shown in FIG. 7. FIG. 7 shows a perspective view of a part of the wearable device 10, namely the housing portion 20, when performing the method of FIG. 6. The housing portion 20 can for example be the housing portion of the wearable device shown in FIG. 5. The housing portion 20 can also comprise an attachment portion on which part of the fastening portion 24 is arranged, in particular the pin fastener as explained with reference to FIG. 5. As can be seen in FIG. 7, the formed housing portion 20 is arranged in an injection mould 30 which is formed such that the elastic material portion 14 can be formed in the second injection moulding step.

In a third step S103, the at least two skin conductance electrodes for contacting skin of the user can be provided or arranged in the elastic material portion 14. Thus, the skin conductance electrodes 12 surround the elastic material portion 14. The step S103 of providing the skin conductance electrodes 12 can also be performed before the second injection moulding step S102.

In a final step S104, the skin conductance measuring unit is then arranged in the wearable device. As can be seen in FIG. 7, the skin conductance measuring unit (electronic circuitry) can be arranged in an open space 31 formed within the housing portion 20. The wristband material part 22 or elastic material portion 14 can be securely and detachably attached to the housing portion 20.

When the wearable device 10 described herein contacts the skin of the user, in particular the wristband contacting the volar side of the wrist of the user, a stabilizing period of several minutes is needed after putting on the wearable device, for example at least 10 minutes or at least 15 minutes. After this stabilization period, the skin conductance values or data are sufficiently high and stable to measure.

Figure 8:
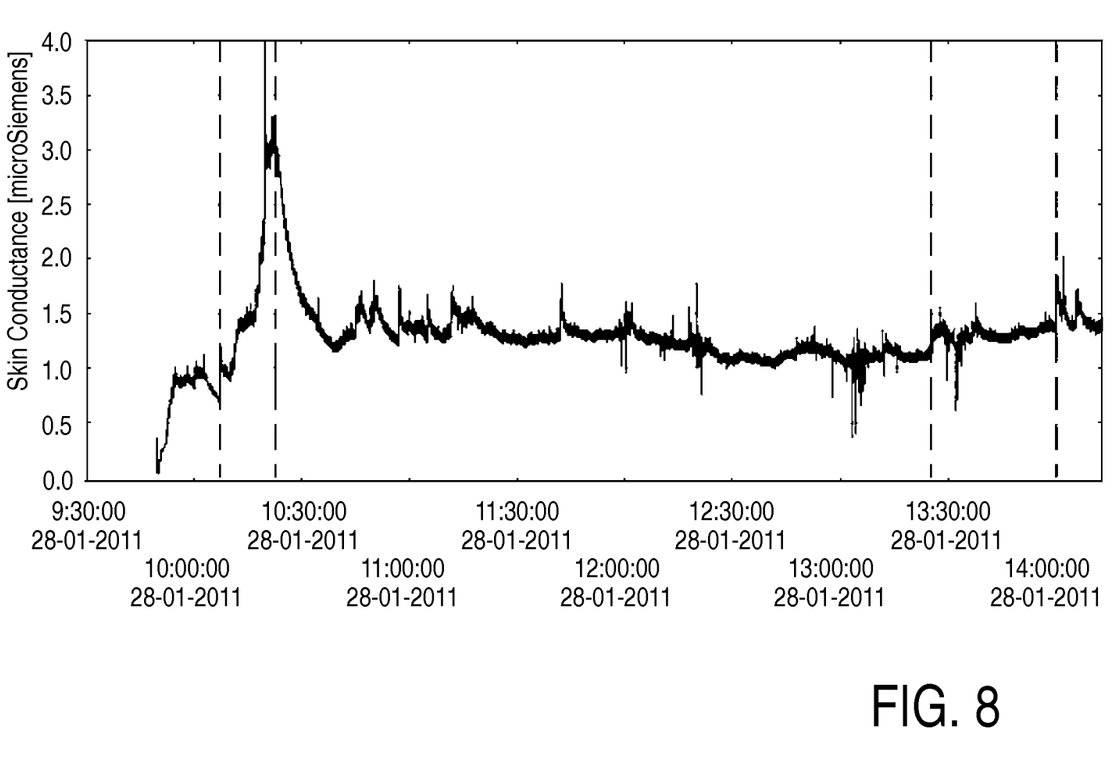
FIG. 8 shows a first example of a skin conductance trace measured with a wearable device according to an embodiment.

FIG. 8 shows a first example of a skin conductance trace measured with the wearable device according to an embodiment, in particular the wearable device 10 described in connection with the previous figures. As can be seen in FIG. 8, the skin conductance values (skin conductance signal) increase about a ten-fold in the first about 10 minutes. After this initial ramp up, the signal variations are caused by the sweat gland activation of the user wearing the wearable device only. The formation of the fluid film is visible in the first about 20 minutes of the skin conductance measurement with the wearable device. The skin conductance value increases sharp in the beginning, and levels off when the fluid film is complete. Therefore, there is a slow down slope of the measured skin conductance value (skin conductance signal), as can be seen in FIG. 8, due to restricted fluid evaporation. For example after a stressful period, the fluid film is causing the skin conductance to be high for a much longer time (e.g. up to about 30 minutes) than the electrodermal response (e.g. about 10 to 20 seconds). The slow decline of the skin conductance value is the result of re-uptake by the stratum corneum of the skin. However, due to the elastic material being non-permeable for gaseous and liquid substances (e.g. rubber), fluid loss by evaporation is reduced or eliminated (or minimized), leaving only the re-uptake by the skin.

Figure 9:
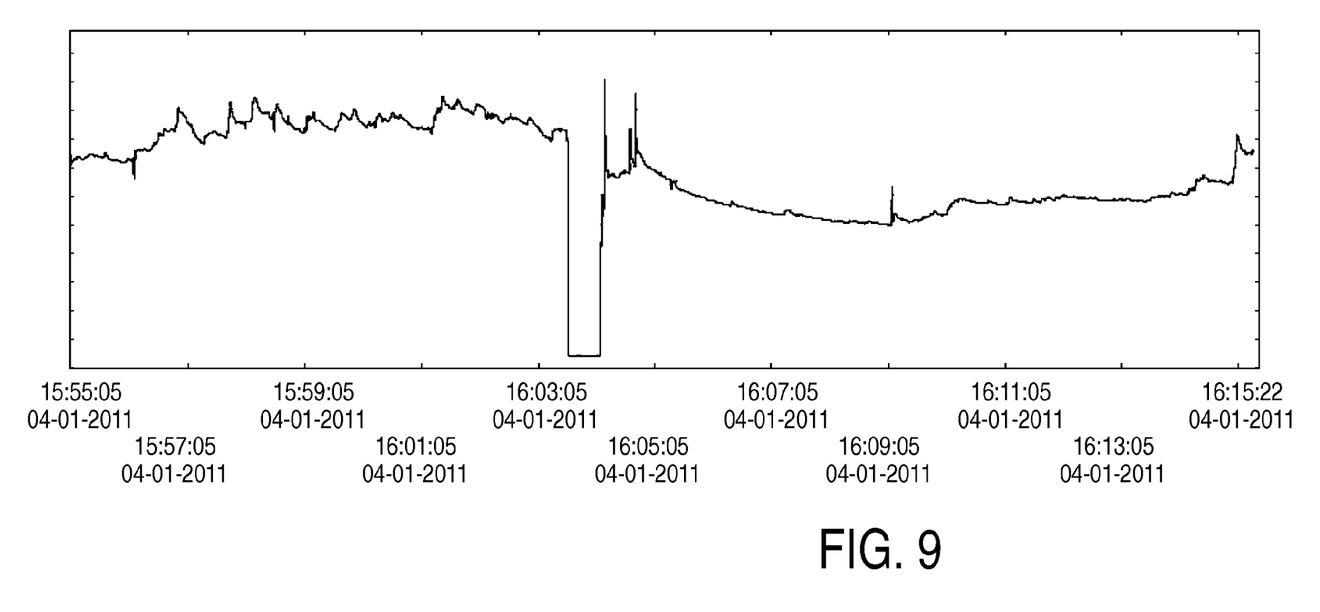
FIG. 9 shows a second example of a skin conductance trace measured with a wearable device according to an embodiment.

FIG. 9 shows a second example of a skin conductance trace measured by the wearable device according to an embodiment, in particular the wearable device 10 as described in connection with the previous figures. In FIG. 9, the wearable device (or wristband) has been removed for about 30 seconds (at a time between about 16:03 and 16:05 o'clock). However, this short break does not affect the skin conductance measurement level after the wearable device is put on again. As can be seen in FIG. 9, the signal is stable after the short duration breach that the wearable device has been removed. This is due to the fact that a stable microclimate as previously explained is built up. This microclimate is caused by skin moisturization due to hermetic sealing. Thus, a short period, for example up to 30 seconds, of taking off the wearable device does not have any affect on the level of skin conductance.

Figure 10:
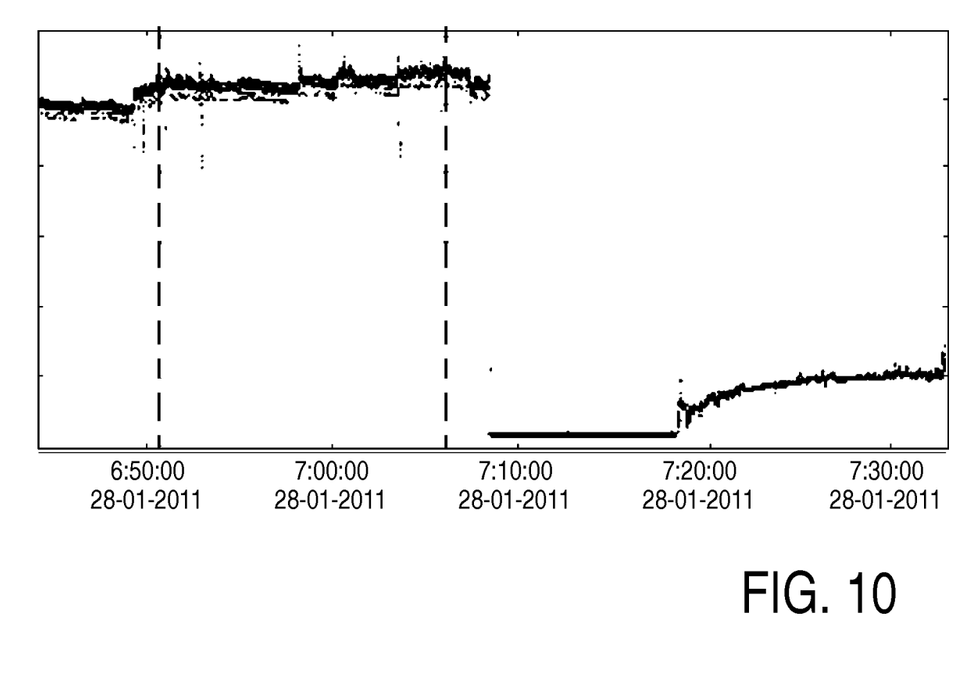
FIG. 10 shows a third example of a skin conductance trace measured with a wearable device according to an embodiment.

FIG. 10 shows a third example of a skin conductance trace measured with the wearable device according to an embodiment, in particular the wearable device as described in connection with the previous figures. In FIG. 10, between about 7:05 and 7:10 o'clock, the user put off the wearable device, took a shower and dried the skin afterwards. Then, the user put on the wearable device again. As can be seen in FIG. 10, the effect of skin dehydration caused by taking a shower and drying the skin afterwards, causes the skin conductance level to drop to its original level from before the skin moisturization due to hermetic sealing.

The profile of the skin conductance ramp up after putting on the wearable device can be modelled. The skin conductance signal can then be corrected for this ramp up effect, to obtain a reliable skin conductance value or signal also in the first minutes after putting on the wearable device.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A wearable device wearable by a user for measuring skin conductance of the user, the wearable device comprising:
   at least two skin conductance electrodes for contacting skin of the user; and
   an elastic material portion designed to form a material surface which surrounds the skin conductance electrodes and a portion of the skin of the user, wherein
      the elastic material portion, when the wearable device is worn by the user, isolates the skin conductance electrodes and the portion of the skin from a surrounding ambient environment by contacting the skin with portions of the elastic material portion on opposite sides of the conductance electrodes, and
      wherein an elastic material of the elastic material portion is non-permeable for gaseous and liquid substances such that the elastic material portion, when the wearable device is worn by the user, causes a fluid film to be generated between the portion of skin and the skin conductance electrodes;
   a housing portion coupled with the at least two skin conductance electrodes and the elastic material portion, wherein the elastic portion is formed from material having a greater elasticity than a material of the housing; and
   a skin conductance measuring unit configured to measure the skin conductance of the user between the skin conductance electrodes, wherein the skin conductance measuring unit is at least partly arranged in the housing portion of the wearable device.

2. The wearable device of claim 1, wherein the elastic material portion is arranged such that an air pocket is sealed off in the vicinity of the skin conductance electrodes, when the skin conductance electrodes contact the skin of the user.

3. The wearable device of claim 1, wherein the elastic material is a polymer or rubber.

4. The wearable device of claim 1, wherein the elastic material is a polyurethane resin mixture at a specific mixture ratio.

5. The wearable device of claim 4, wherein the polyurethane resin mixture is made of polyetherpolypol and 4,4'-diphenylmethane diisocyanate at a ratio of about 100:40.

6. The wearable device of claim 1, wherein the skin conductance electrodes protrude from the material surface.

7. The wearable device of claim 6, wherein the skin conductance electrodes protrude between 100 to 700 micrometers from the material surface.

8. The wearable device of claim 1, wherein the housing portion is made of a non-elastic material.

9. The wearable device of claim 1, wherein the elastic material of the elastic material portion is a polyurethane resin mixture at a specific mixture ratio, and wherein the housing portion is made of the same polyurethane resin mixture at a different mixture ratio.

10. The wearable device of claim 1, wherein the elastic material has an elasticity that is sufficient to follow the shape of the wrist of the user.

11. A method of manufacturing a wearable device wearable by a user for measuring skin conductance of the user, the method comprising:
    providing at least two skin conductance electrodes for contacting skin of the user; and
    forming an elastic material portion designed to form a material surface which surrounds the skin conductance electrodes and a portion of the skin of the user, wherein the elastic material portion, when the wearable device is worn by the user, isolates the skin conductance electrodes and the portion of the skin from a surrounding ambient environment by contacting the skin with portions of the elastic material portion on opposite sides of the conductance electrodes, and
    wherein an elastic material of the elastic material portion is non-permeable for gaseous and liquid substances such that the elastic material portion, when the wearable device is worn by the user, causes a fluid film to be generated between the portion of skin and the skin conductance electrodes;
    forming a housing portion coupled with the at least two skin conductance electrodes and the elastic material portion, wherein the elastic portion is formed from material having a greater elasticity than a material of the housing; and
    providing a skin conductance measuring unit configured to measure the skin conductance of the user between the skin conductance electrodes, wherein the skin conductance measuring unit is at least partly arranged in the housing portion of the wearable device.

12. The method of claim 11, wherein the housing portion is formed from a non-elastic material.

13. The method of claim 11, wherein the elastic material portion is formed by injection moulding.

* * * * *